US 6,619,103 B1

(12) United States Patent
Cardinale et al.

(10) Patent No.: US 6,619,103 B1
(45) Date of Patent: Sep. 16, 2003

(54) SAMPLE FLOW PATH ASSEMBLY FOR ELECTRONIC GAS LEAK DETECTORS

(75) Inventors: Dennis Cardinale, Plantation, FL (US); Manuel Duarte, Hallandale, FL (US)

(73) Assignee: Advanced Test Products, Inc., Miramar, FL (US)

( * ) Notice: Subject to any disclaimer, the term of this patent is extended or adjusted under 35 U.S.C. 154(b) by 0 days.

(21) Appl. No.: 10/082,784

(22) Filed: Feb. 25, 2002

(51) Int. Cl.[7] .......................... G01M 3/04; G01N 7/00; G01N 1/14
(52) U.S. Cl. .................... 73/40.7; 73/31.02; 73/864.34; 73/864.81
(58) Field of Search .............................. 73/40.7, 31.01, 73/31.02, 864.35, 864.73, 864.34, 864.81, 23.2

(56) References Cited

U.S. PATENT DOCUMENTS

| | | | | |
|---|---|---|---|---|
| 3,311,455 A | * | 3/1967 | Robinson | 422/97 |
| 3,768,300 A | * | 10/1973 | Nemeth | 73/23.26 |
| 3,786,675 A | * | 1/1974 | Delatorre et al. | 73/40.7 |
| 4,369,647 A | * | 1/1983 | Shigemori et al. | 73/25.03 |
| 4,488,118 A | * | 12/1984 | Jeffers et al. | 324/455 |
| 4,879,546 A | * | 11/1989 | Dunham et al. | 340/632 |
| D319,596 S | * | 9/1991 | Krolopp | D10/81 |
| 5,347,223 A | * | 9/1994 | Krcma et al. | 324/455 |
| 5,351,037 A | * | 9/1994 | Martell et al. | 340/632 |
| 5,889,199 A | * | 3/1999 | Wong et al. | 73/40.7 |
| 6,362,741 B1 | * | 3/2002 | Hickox et al. | 73/40.7 |

OTHER PUBLICATIONS

D–TEK Refrigerant Leak Detector User's Manual, Leybold Inficon, (19 pages), 1998 (no month).
D–TEK Refrigerant Leak Detector User Guide, Leybold Inficon, (19 pages), 1995 (no month).
TOP GUN™, H10Xpro Refrigerant Leak Detector Operation Manual, Yokogawa Corporation of America, Feb. 2000.
BACHARACH® The Informant™ Refrigerant Leak Detector Instruction 19–9210 Operation & Maintenance, Rev. 4—Apr. 2001.

* cited by examiner

Primary Examiner—Edward Lefkowitz
Assistant Examiner—Michael Cygan
(74) Attorney, Agent, or Firm—Baker & Hostetler LLP; Dennis P. Cawley

(57) ABSTRACT

A gas detector having a sample flow path assembly capable of providing a sample air flow rate to a sensing device in excess of about 300 SCCM. The sample flow path assembly also provides the gas detector with a short signal path between the sensing device and a printed circuit board, an efficient sample path, and ready access to and easy replacement of the sensing device as well as easy replacement of the probe, making the gas detector generally more reliable and cost effective. The sample path assembly requires a simple method of construction and sensing device replacement thereby reducing the difficulty and the time required for manufacturing the sample flow path assembly and, ultimately, reducing the cost of manufacturing the leak detector.

18 Claims, 10 Drawing Sheets

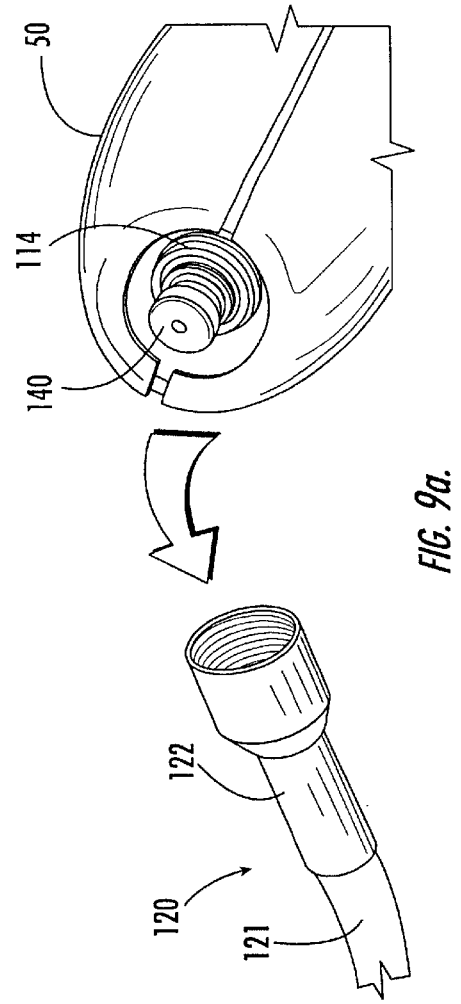
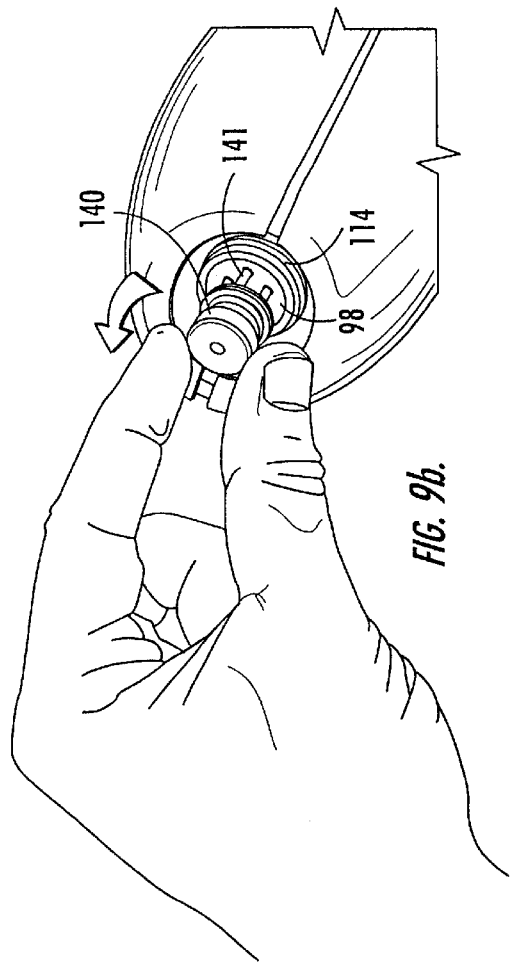
FIG. 9a.
FIG. 9b.

SAMPLE FLOW PATH ASSEMBLY FOR ELECTRONIC GAS LEAK DETECTORS

BACKGROUND OF THE PRESENT INVENTION

1. Field of the Present Invention

The present invention relates generally to the field of gas detectors, and, in particular, to the art of supplying sample air to one or more heated electrode sensing devices to detect halogenated refrigerants.

2. Background Art

Electronic refrigerant leak detectors typically include a power supply, such as a replaceable or rechargeable battery, one or more sensing devices (sensors), a printed circuit board and a sample path assembly for drawing air into or across the sensing device. The sample path of most electronic refrigerant leak detectors start at a flexible hollow tube of varying length called a goose-neck probe. The free end of the probe is positioned where the operator wants to take an air sample. The sample of air is drawn into the free end of the probe, through a filter, and then across or past the sensing device before being exhausted from the detector. The detector generally has some means for drawing the sample of air along the sample path, for example a fan or pump.

Currently available electronic refrigerant leak detectors include the "D-TEK," manufactured by Leybold-Inficon, headquartered in East Syracuse, N.Y.; "The Informant," manufactured by Bacharach, headquartered in Pittsburgh, Pa.; and the H10Xpro "Top Gun," manufactured by Yokogawa Corporation of America, headquartered in Newnan, Ga. Each detector has a gooseneck probe extending some length from the detector body and a means for drawing an air sample through the probe. The air sample is drawn through or across the sensor which is electronically connected to a printed circuit board that is disposed within the interior of the detector body.

The D-TEK uses a centrifugal fan surrounded by a shroud to draw air through a probe. One end of the flexible goose-neck probe is glued to the shroud while the free end extends about 16 inches from the detector body. A sensor is located within the free end of the flexible probe. The fan draws the air sample through the free end of the probe, across the sensor, through the remaining length of the probe and into the shroud before it is exhausted from the fan. Signals from the sensor are transmitted to the printed circuit board via electrical wires inserted into the probe and traveling the length of the probe from the sensor to the printed circuit board. The wires are inserted through a rubber plug that seals the shroud where the probe is attached so that leaks around the wires are minimized. A probe tip, attached to the free end of the flexible probe, encloses the sensor. The sample flow rate across the sensor is approximately 35 standard cubic centimeters per minute (SCCM).

Unfortunately, this construction has several disadvantages concerning the manufacture and use of the detector. The relatively low flow rate across the sensor results in a low sensor sensitivity, a longer response time and a longer clearing time (the amount of time required to purge the sample path assembly and the sensor of previously analyzed gas so that a new sample can be taken and analyzed). The flexible probe is glued to the fan shroud, which makes the replacement of a damaged flexible probe difficult and time consuming. The wires connecting the sensor to the printed circuit board are inside the flexible probe, and hence, obstructs the flow path between the probe tip and the fan, potentially resulting in an unquantifiable and unpredictable resistance to the flow of the air sample through the flexible probe, ultimately causing an inconsistent sample flow across the sensor from one use to the next and from one detector to the next. Besides obstructing the flow path, the length of the wires connecting the sensor and the printed circuit board increases the electrical resistance of the wires, increasing demand on the battery and reducing the operating time of the detector without changing batteries or recharging the existing battery. Finally, inserting wires through the small diameter flexible tubing of the flexible probe, sealing the flow path around the wires, and gluing the flexible probe to the fan shroud all increase the difficulty and time required to manufacture the sample path assembly of the detector and to replace the probe or fan if either are damaged.

Like the D-TEK, "The Informant" uses a fan surrounded by a shroud to draw air through a 20 inch flexible probe. One end of the flexible probe is glued to the shroud and the free end is covered by a probe tip. The sensor is located within free end of the flexible probe. The sensor is covered by the probe tip and a filter. Wires connecting the sensor to the printed circuit board are routed through the shroud and into the interior of the flexible probe. A flexible sealant is used to seal the shroud and flexible probe around the wires. The typical flow rate is approximately 50 SCCM. The Informant has many of the same disadvantages as the D-TEK. In addition, the use of a flexible sealant increases the time for manufacture because the sealant must be "cured" to create a usable seal.

The "Top Gun" detector offers a different approach to constructing a sample path assembly for an electronic refrigerant leak detector. The sensor is connected directly (i.e., is soldered) to the printed circuit board, eliminating the wires found in the flow paths of the D-TEK and The Informant. A flexible probe is approximately 16 inches long and is removably attached to the detector body. A rotary vane pump draws air through the flexible probe at a flow rate of approximately 250 SCCM. The air sample travels through the flexible probe, into the inlet of the rotary vane pump, through the pump to the outlet of the pump, and through a 'T' split before encountering the sensor. The air sample from the outlet of the pump is split into two paths at the 'T' split—one path is exhausted from the detector and one path continues to the sensor. Thus, while the flow rate through the flexible probe and rotary vane pump is about 250 SCCM, the actual flow rate of the air sample across the sensor is considerably less and is approximately equivalent to the flow rate of the air sample across the sensors in the D-TEK and The Informant.

The removable flexible probe of the Top Gun, which makes replacement easy, is advantageous over the D-TEK and the Informant. Furthermore, unlike the D-TEK and The Informant, there are no wires traveling the length of the probe to connect the sensor to the printed circuit board. This results in a reduced demand on the battery and an unobstructed flow through the flexible probe. Unfortunately, however, the construction of the sample flow path assembly of the Top Gun presents other disadvantages, most notably the inaccessibility of the sensor, which is fixedly attached to the printed circuit board located inside the detector. This inaccessibility makes replacement of the sensor extremely difficult. Another disadvantage is the placement of the sensor on the outlet side of the pump which introduces potential mixing problems associated with the air sample within the pump, and an increase in the clearing time. Further, because of the flow split, the increased flow rate through the flexible probe results in an increased demand on the battery by the pump without an appreciable increase in sensor sensitivity.

The reduced flow rate across the sensor is a necessary component of the "Top Gun" design. Otherwise, the sensor may be damaged if subjected to the full, high, flow rate. Finally, the additional tubing within the detector body required for the 'T' split increases the number of steps needed to manufacture the flow path assembly, thereby increasing the difficulty and time required.

For greatest detector efficiency, the sensitivity of the sensing device (sensor) must be maximized to an optimum level, the response time of the sensing device should be minimized, and the time needed to clear the detector of already sampled gas (the clearing time) must be minimized, all while maintaining a reasonable demand on the power supply (usually measured in terms of battery life). One, way to maximize the sensitivity of the sensing device is to increase the flow rate of the air sample flowing across or past the sensing device. The clearing time can be minimized by shortening the sample path between the probe tip and the sensing device and/or increasing the flow rate so the sampled air is exhausted from the detector more quickly. The response time may be minimized by increasing the flow rate of the air sample or shortening the signal path between the sensing device and the electronic circuit. Battery life may be maintained in a variety of ways, including shortening the signal path between the sensing device and electronic circuit, thereby reducing the resistance losses of the wires connecting the sensing device to the electronic circuit, or by reducing the demand placed on the battery by the pump or the fan, either by operating at a lower flow rate or providing a more efficient sample path.

Thus, mindful of the disadvantages of many of the currently available electronic refrigerant leak detectors, a need exists for a gas leak detector that has a sample flow path that maximizes sensing device sensitivity, minimizes respond time, and minimizes clearing time, all while maximizing battery life and reducing manufacturing difficulty and time.

SUMMARY OF THE INVENTION

Briefly summarized, the present invention relates to a sample flow path assembly for use in a gas detector that is capable of sensing the presence of at least one predetermined gas and that has a temperature controlled sensing device, a bias current controlled sensing device, or a combination thereof. The sample flow path assembly includes a means for generating a sample air flow past the sensing device at a flow rate in excess of about 300 SCCM and means for conducting the sample air flow past the sensing device.

The means for generating a sample air flow is a pump that has an inlet port and an outlet port. The pump is located within a body of the gas detector. The means for conducting the sample air flow past the sensing device includes a socket connected to the inlet port of the pump, a collar located at one end of the housing and surrounding the socket, and a probe attached to the collar whereby the probe extends beyond the housing of the detector to open to the surrounding environment. The sensing device is disposed upon and supported by the socket such that the sensing device is disposed between the probe and the pump. A flexible interconnect connects the sensing device to a printed circuit board. The pump motor may be electrically connected to the printed circuit board and supplied DC power, preferably by a battery.

BRIEF DESCRIPTION OF THE DRAWINGS

Further features, embodiments, and advantages of the present invention will become apparent from the following detailed description with reference to the drawings, wherein:

FIGS. 9a–9d are sequential views of a method to replace the sensing device disposed within the sample flow path assembly embodied by the present invention.

DETAILED DESCRIPTION OF THE PREFERRED EMBODIMENTS

Figure 1:
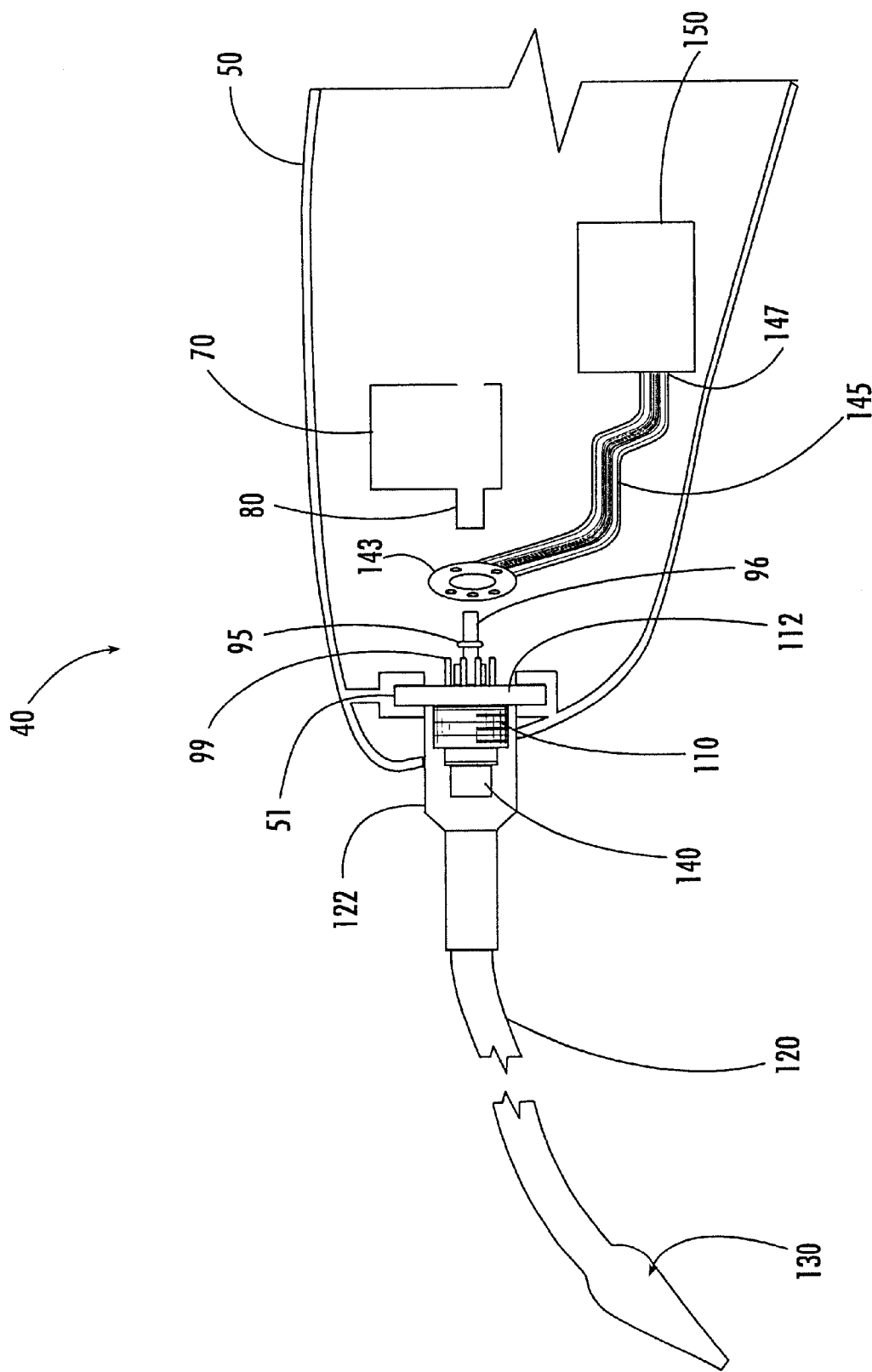
FIG. 1 is a diagrammatic view of the sample flow path assembly embodied by the present invention.
Figure 2:
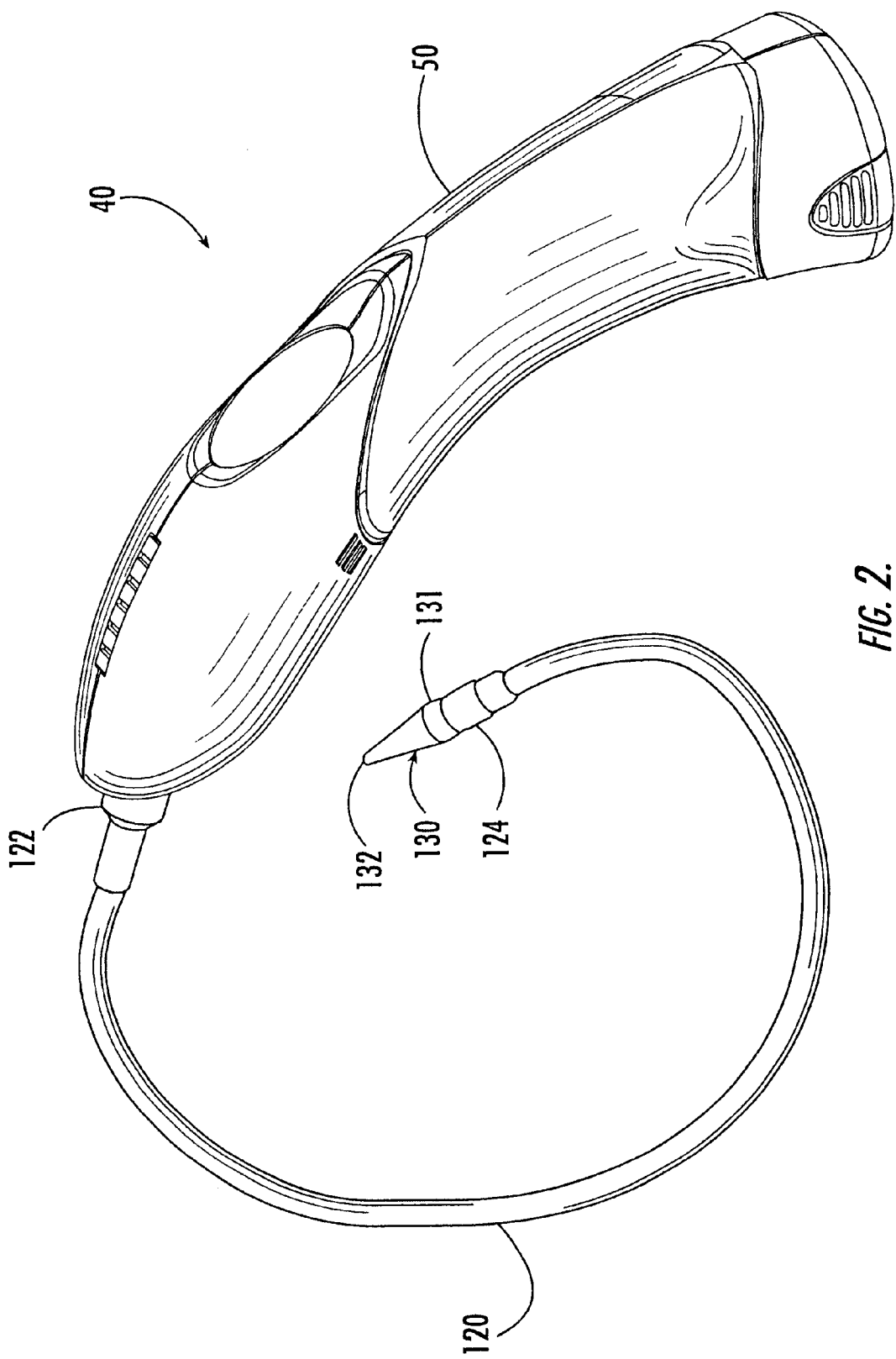
FIG. 2 is a perspective of a gas detector using the present invention.

An electronic gas leak detector 40 has a body 50, a sample flow path assembly 55, a printed circuit board 150, control apparatus (not shown) and a power supply (not shown). Referring now to the drawings, in which like numerals represent like components throughout the several views, the sample flow path assembly 55, has an internal subassembly, comprising a pump 70, a socket 90, a collar 110, and a flexible interconnect 145. The sample flow assembly 55 also includes a sensing device 140 and a probe 120.

Figure 4:
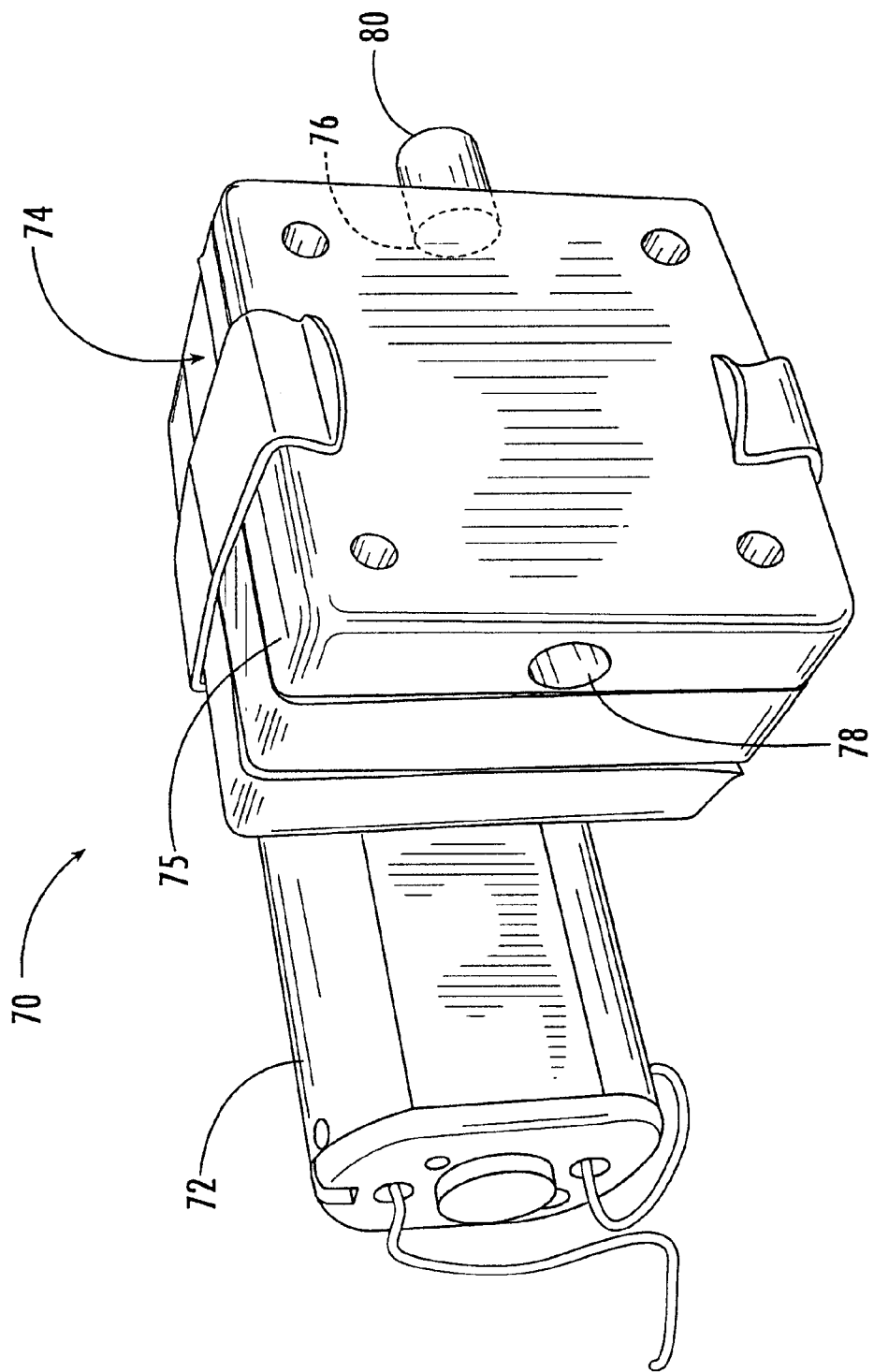
FIG. 4 is a perspective of the pump shown in FIG. 3.
Figure 6:
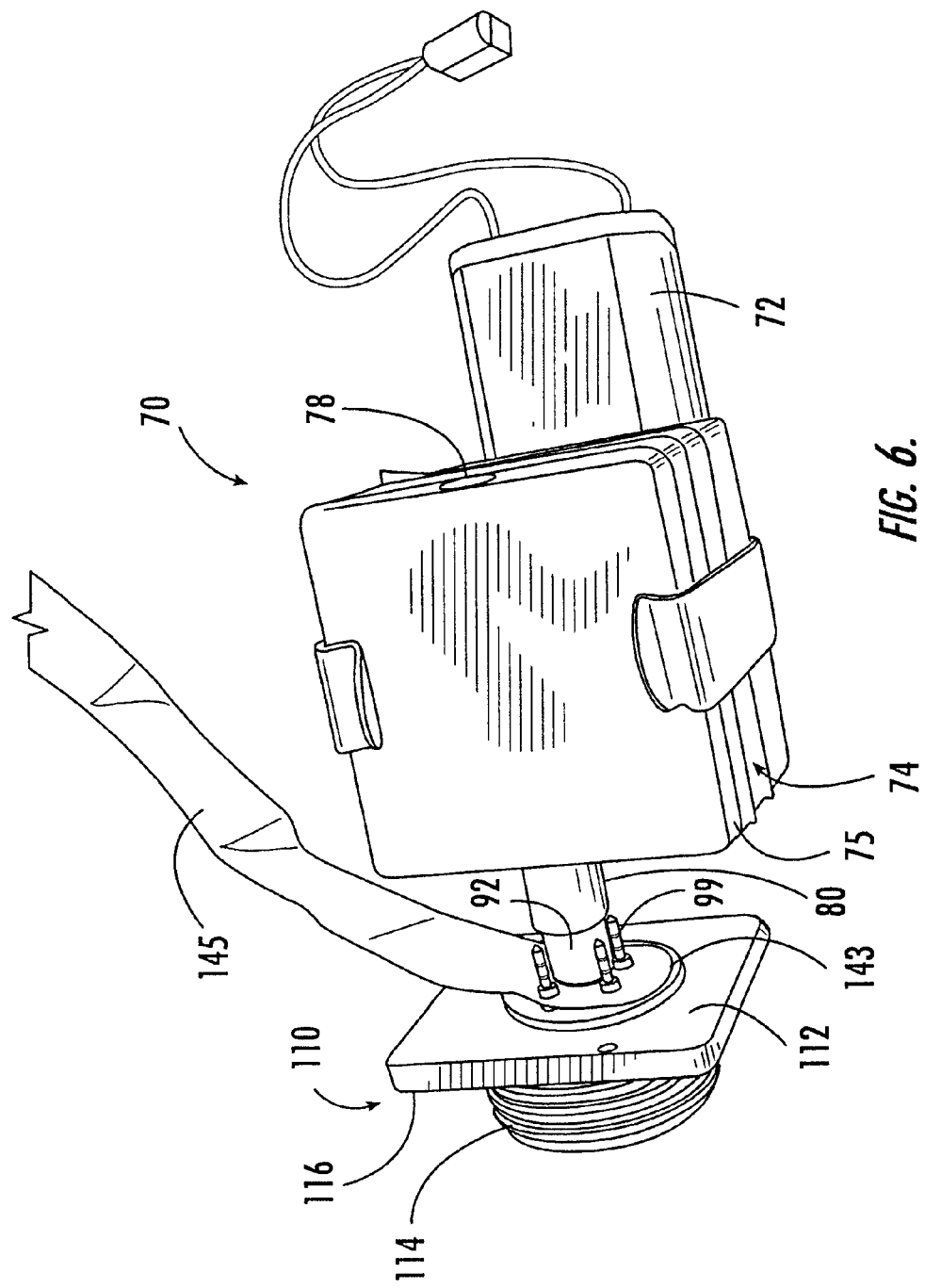
FIG. 6 is a perspective of the internal subassembly of the sample flow path assembly.
Figure 7:
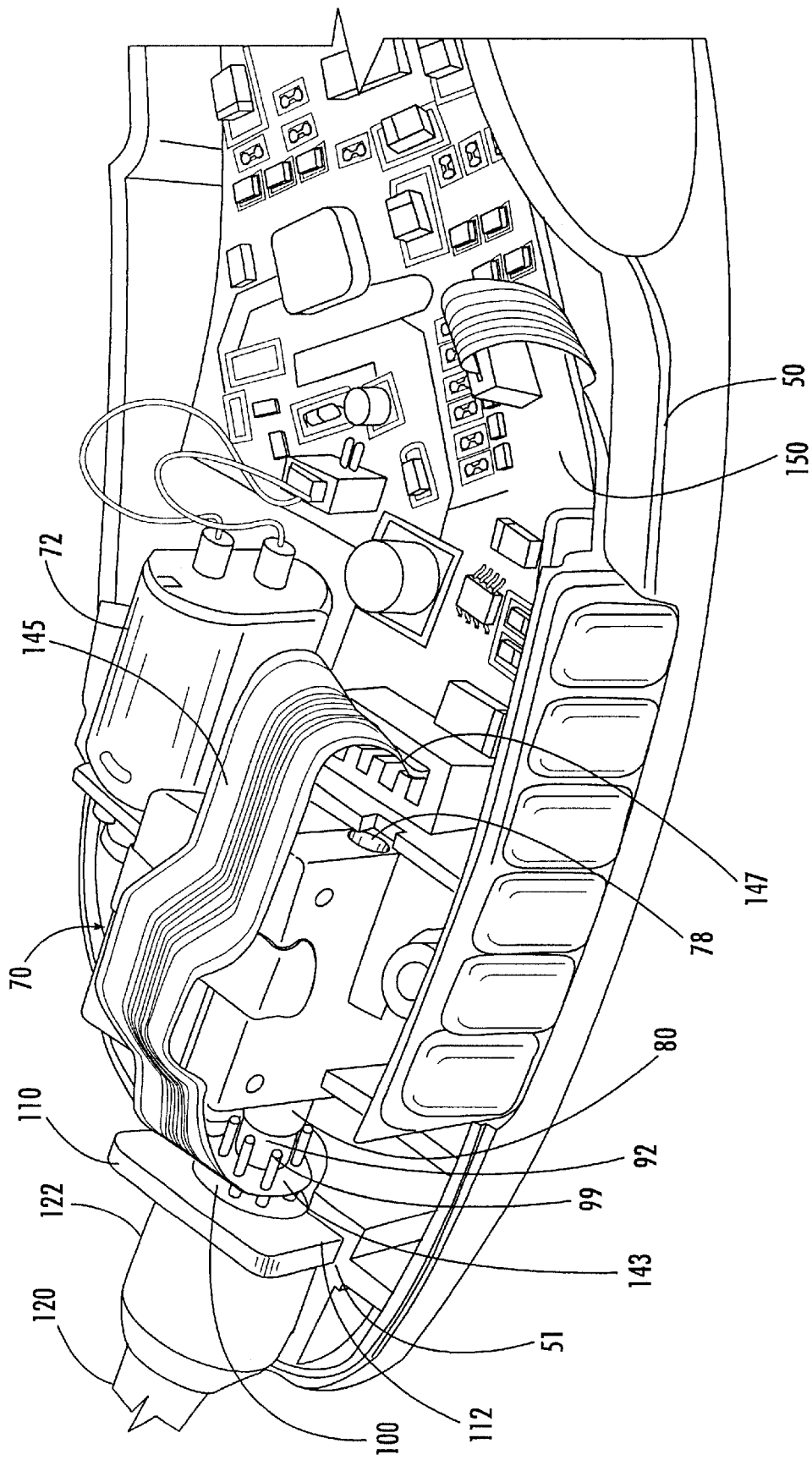
FIG. 7 is a cut away view of a gas detector showing the relative placement of the components of the present invention within and without the detector body.
Figure 8:
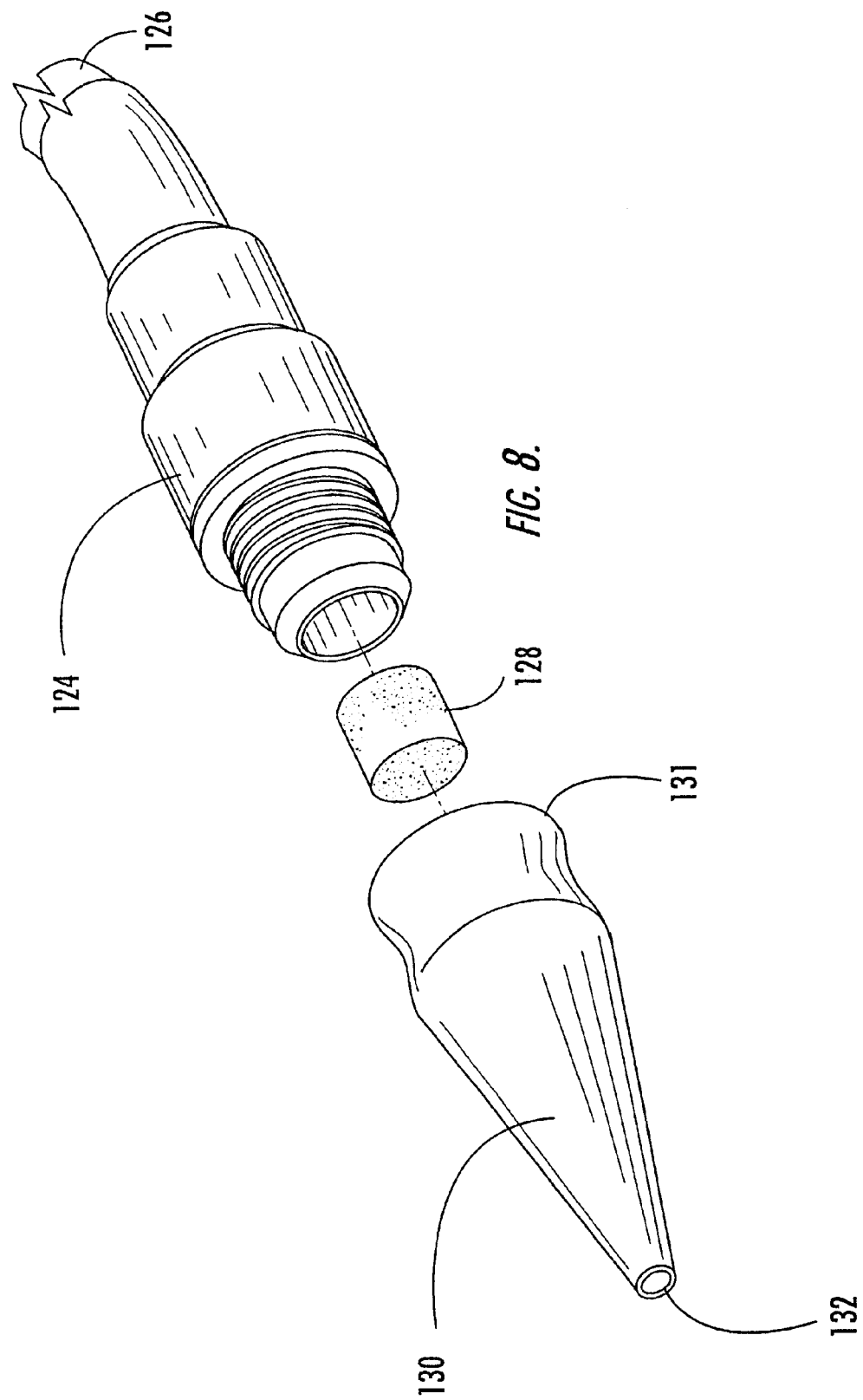
FIG. 8 is an exploded view of the probe and probe tip portion shown in FIG. 3.

Referring to FIG. 4, the pump 70 is a diaphragm pump suitable for pumping gases at unrestricted flow rates in excess of 400 SCCM. The pump 70 includes a motor 72 attached to a pump body 74. Air enters the pump body 74 through an inlet port 76 disposed on a manifold 75 and exits the pump body 74 through an outlet port 78 disposed on the manifold 75. In the present invention, the inlet port 76 and the outlet port 78 are located on opposite sides of the manifold 75. This construction results in a direct sample flow path to the inlet port 76 of the pump 70 when the pump 70 is positioned within the body 50 of the detector 40. This direct path eliminates the necessity of lengthy runs of tubing inside the body 50 of the detector 40, thereby creating a more efficient flow path. Further, the placement of the inlet and outlet ports 76, 78 on opposite sides of the manifold 75 creates a more compact unit so that the pump 70 can be easily installed within the body 50 of the detector 40, as shown in FIGS. 6 and 7. In a preferred embodiment, the pump 70 is a diaphragm micro-pump manufactured by Anglo Nordic Burner Products Ltd. of West Molesey, Surrey, England, identified as part number AN7400101, which is capable of unrestricted air flow rates up to 800 SCCM. The factory provided manifold of the Anglo Nordic pump, which has the inlet and outlet ports on its outer face, has been modified such that the inlet port 76 is on one side of the manifold and the outlet port 78 is on the opposite side of the manifold 75. A duct 80 having a circular cross-section projects outwardly from the inlet port 76.

The socket 90 includes a stem 92 molded to a body 94. The stem 92 is formed from a hollow cylinder. A first stem segment 96 opposite the body 94 has an outer diameter smaller than that of the portion of the stem 92 that is molded to the body 94 of the socket 90. The first stem segment 96 is of the size such that it can be inserted into the duct 80 of the inlet port 76 of the pump 70. An O-ring 95 fits around the first stem segment 96 and is used to seal the connection between the first stem segment 96 and the duct 80, providing a leakage free direct connection between the socket 90 and the pump 70.

Figure 3:
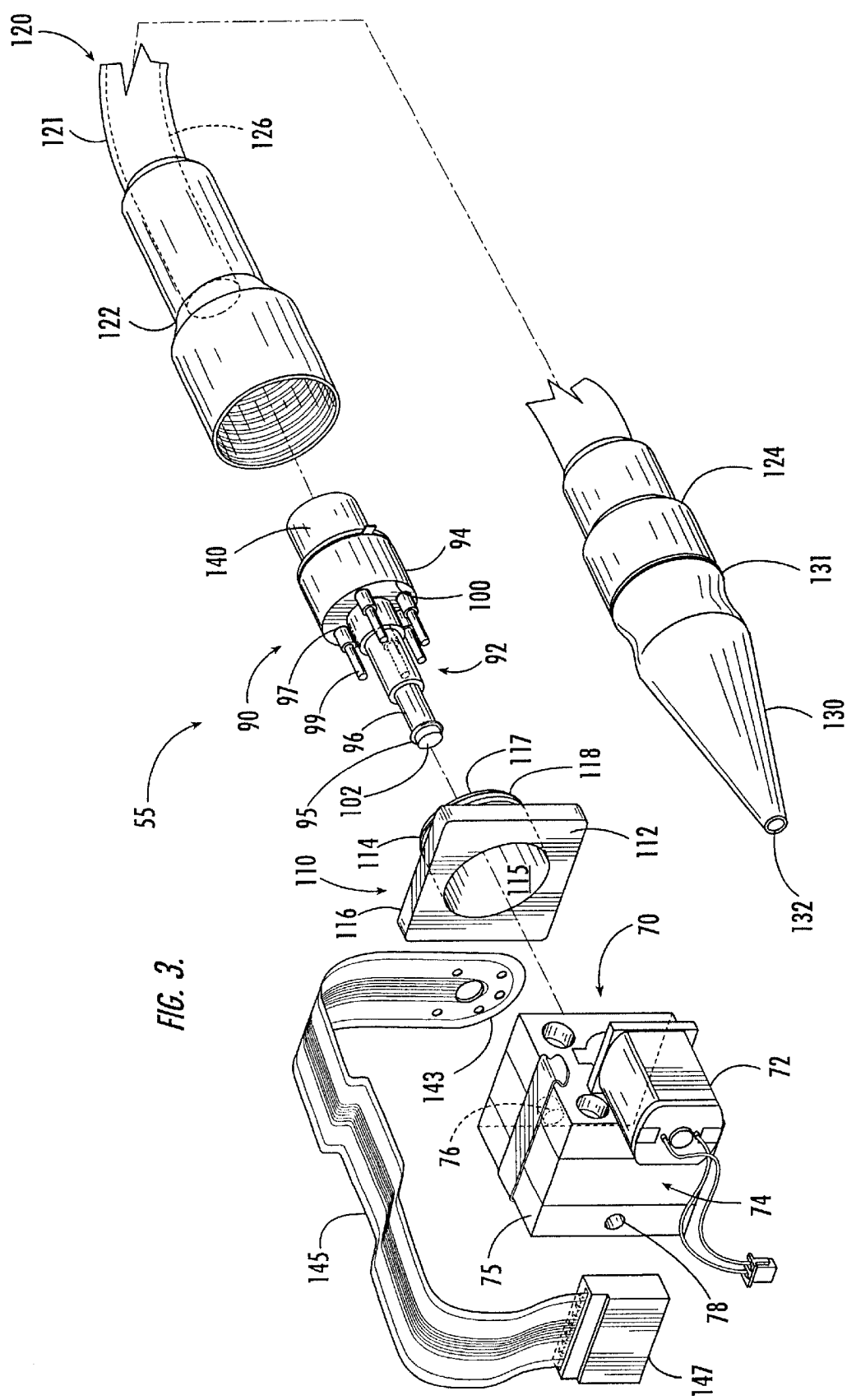
FIG. 3 is an exploded view of the sample flow path assembly embodied by the present invention with the sensing device being shown disposed with the sample flow path.
Figure 5:
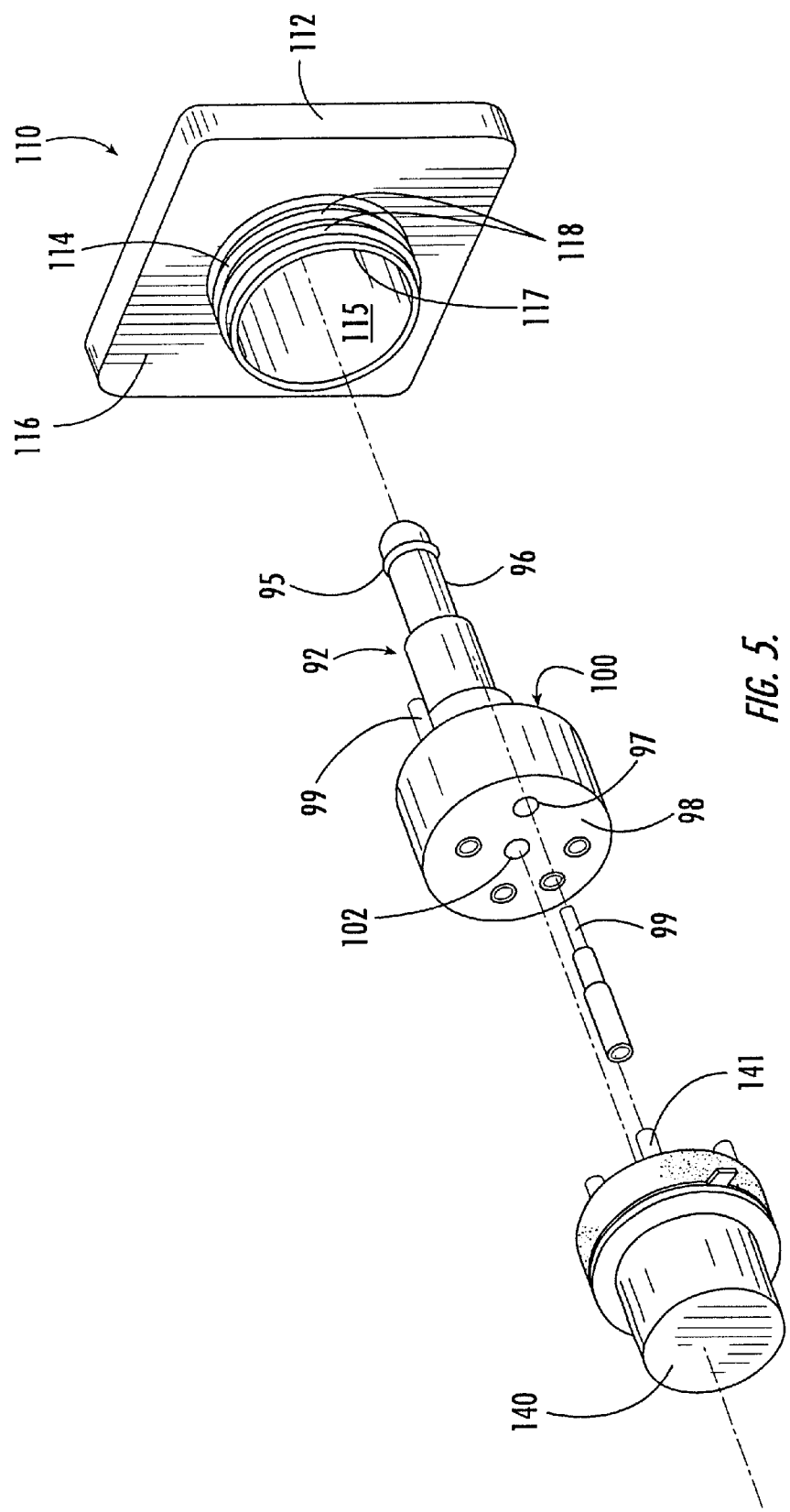
FIG. 5 is an exploded view of the collar and socket components and the sensing device shown in FIG. 3.

Referring to FIGS. 3 and 5, the socket body 94 is a solid cylinder having a front face 98 and a back face 100. The stem 92 is molded onto the back face 100 of the body 94. A plurality of pin holes 97, extend between the front face 98 and the back face 100 of the body 94 and are spaced upon the faces intermediate a center and an outer surface of the body 94. In a preferred embodiment, five pin holes 97 extend in parallel arrangement between the faces of the body 94. Hollow, electrically conductive pin receptacles 99 are disposed within the pin holes 97, one end in alignment with the front face 98. The pin receptacles 99 continue through the body 94 and protrude beyond the back face 100, external to the stem 92. In a preferred embodiment, the protruding portion of the pin receptacles 99 are parallel to the stem 92 of the socket 90. A sample flow hole 102 extends through the center of the body 94 from the front face 98 to the back face 100, and continues through the stem 92 of the socket 90, creating a continuous sample flow path from the front face 98 of the socket 90 to the duct 80 of the inlet port 76 of the pump 70. The socket 90 is made of an electrically non-conductive, structural material. In a preferred embodiment, the socket 90 is made of plastic.

The collar 110 has a cylindrical portion 114 projecting from and centered upon a front face 116 of a generally rectangular plate 112. An opening 115 extends from a front end 117 of the cylindrical portion 114 through the plate 112. The edges of the plate 112 extend laterally beyond the outer surface 118 of the cylindrical portion 114 so that the opposite sides of the plate 112 engage mating channels 51 formed in the body 50 of the detector 40 as shown in FIG. 7. The outer surface 118 of the cylindrical portion 114 is threaded. A thin washer (not shown) is disposed against the front face 116 of the plate 112 surrounding the cylindrical portion 114. The collar 110 is made from a structurally sound material. In a preferred embodiment, the collar 110 is made of nickel-plated brass.

The socket body 94 is of the size to be inserted into the opening 115 in the collar 110 with the front face 98 of the socket body 94 in approximate alignment with the front end 117 of the cylindrical portion 114 of the collar 110 and the stem 92 protruding beyond the plate 114.

Returning to FIG. 3, the flexible interconnect 145 is a flat electronic cable for electrically connecting two electronic devices for sending and receiving signals therebetween. In the present invention, the flexible interconnect connects the sensing device 140 and the printed circuit board 150. The flexible interconnect has a first end 143 and a second end 147. As shown in FIGS. 6 and 7, the first end 143 of the flexible interconnect 145 is affixed to the pin receptacles 99 protruding from the socket body 94. The second end 147 of the flexible interconnect 145 may be removably attached to the printed circuit board 150. The flexible interconnect 145 is external to the socket 90, and hence external to the sample flow path, eliminating the obstruction in the sample flow path existing in the D-TEK and The Informant refrigerant leak detectors as discussed above. In a preferred embodiment, the first end 143 of the flexible interconnect 145 is soldered to the pin receptacles 99.

Returning to FIG. 5, a sensing device 140 suitable for use with the present invention is disclosed in U.S. patent application Ser. No. 09/838169, filed on Apr. 19, 2001, and incorporated herein by reference. The sensing device 140 has pin receptacles 141 that can be inserted into the pin receptacles 99 on the front face 98 of the socket body 94, thereby connecting the sensing device 140 to the printed circuit board 150 via the flexible interconnect 145.

The probe 120 includes a flexible outer tube 121, an inner tube 126 which may be formed from TEFLON®, a filter 128 and a probe tip 130. The flexible outer tube 121 has a first bushing 122 at one end and a second bushing 124 at an second, opposite end. The first bushing 122 is threaded such that it may be removably attached to the cylindrical portion 114 of the collar 110. The inner tube 126 is fastened to the first bushing 122 and is long enough to extend the length of the flexible outer tube 121, terminating at the second bushing 124. The filter 128, preferably made of foam, is inserted into the second bushing 124 and rests on the inner tube 126. The probe tip 130 is shaped like a funnel, with a first end 131 and a second end 132, the first end 131 having a larger diameter than the second end 132. The first end 131 is threaded so that it may be removably attached to the second bushing 124. The second end 132 of the probe tip 130 has an opening so that an air sample can be drawn in through the second end 132 of the probe tip 130, through the probe 120, past the sensing device 140 and into the duct 80 of the inlet port 76 of the pump 70. The probe tip 130 is made of a structural material. In a preferred embodiment, the probe 120 is approximately 14 inches long and the probe tip 130 is made of aluminum. One feature of the present invention is to have the probe 120 be a flexible goose-neck probe. Although a preferred embodiment of the present invention includes a probe 120 that is flexible, it is readily understood that a semi-rigid or a rigid probe may be used instead.

The sample flow path assembly 55 is constructed in two phases—first constructing and installing the internal subassembly into the body 50 of the detector 40 then attaching the external elements (i.e., the sensing device 140 and the probe 120) to the internal subassembly. To begin construction of the internal subassembly, the pin receptacles 99 are press fit into the pin holes 97 disposed within the socket body 94. The socket body 94 is then press fit into the opening 115 in the collar 110 with the front face 98 of the socket body 94 in approximate alignment with the front end 117 of the cylindrical portion 114 of the collar 110. The first end 143 of the flexible interconnect 145 is soldered to the portion of the pin receptacles 99 protruding from the back face 100 of the socket body 94. The O-ring 95 is fitted over the first stem segment 96 which is then inserted into the duct 80 of the inlet port 76 of the pump 70 sealing the connection between the first stem segment and the duct. The washer is placed around the cylindrical portion 114 and against the plate 112 of the collar 110. The completed internal subassembly is then installed into one half of the detector body 50 which also holds the printed circuit board 150 and the controls, as shown in FIG. 7. The second end 147 of the flexible interconnect 145 and the pump motor 72 are connected to the printed circuit board 150. The other half of the detector body 50 is placed in position and the two halves of the detector body are fastened together, enclosing the internal subassembly, leaving an opening through which the front face 98 of the socket 90 and the surrounding cylindrical portion 114 of the collar 110 can be accessed. The sensing device 140 is pressed onto the front face 98 of the socket body 94, the pins of the sensing device 140 engaging the pin receptacles 99 disposed in the body 94 of the socket 90. The filter 128 is inserted into the free end 123 of the flexible outer tube 121 and the probe tip 130 is then threaded onto the second end bushing 124, completing assembly of the of the probe 120. The first end bushing 122 is threaded over the threaded outer surface 118 of the cylindrical portion 114 of the collar 110 and tightened, attaching the probe 120 to the internal subassembly of the sample flow path assembly 55. The power supply is connected to the body 50 of the detector 40, thus completing the assembly of the gas leak detector 40.

Figure 9C:
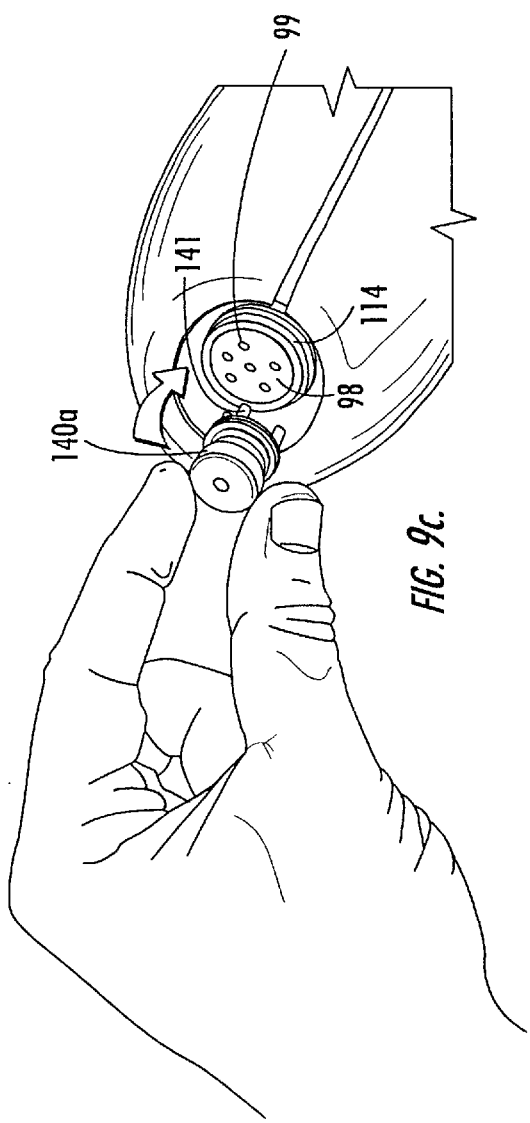
Figure 9D:
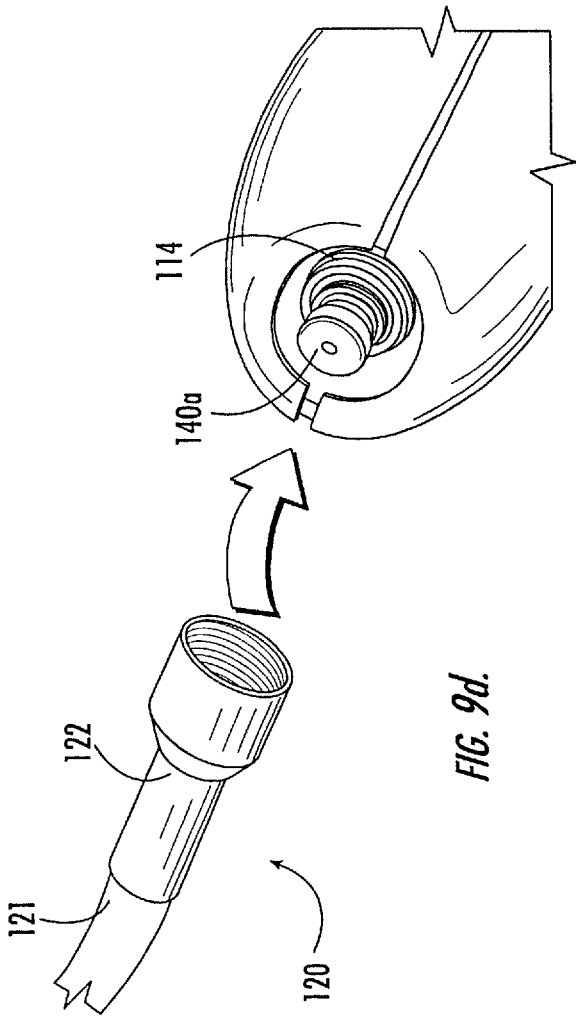

Replacement of the sensing device 140, as illustrated in FIGS. 9a–9d, may be accomplished by detaching the probe 120 from the cylindrical portion 114 of the collar 110 (FIG. 9a), removing the installed sensing device 140 from the socket body 94 (FIG. 9b), pressing a replacement sensing device 140a onto the front face 98 of the body 94 of the socket 90, making sure the pins 141 of the sensing device 140a engage the pin receptacles 99 disposed in the body 94 (FIG. 9c), and reattaching the probe 120 to the cylindrical portion 114 of the collar 110 (FIG. 9d). With a preferred embodiment, replacement of the sensing device 140 can be accomplished without the use of tools.

Likewise, the probe 120 may be replaced by detaching the existing probe 120 from the collar 110 and attaching a replacement probe. Again, in a preferred embodiment, the replacement steps can be accomplished without the use of tools. In like manner, the pump 70 and the socket 90 and collar 110 combination may be replaced.

Revisiting the requirements of greater sensing device sensitivity, shorter response time, shorter clearing time and reasonable battery life, the present invention has the advantages of a higher air flow rate, a more efficient sample flow path, and a short signal path between the sensing device and the printed circuit board.

The present invention has a sample air flow past the sensing device at a flow rate in excess of 300 SCCM, which is at least six times greater than the flow rate of "The Informant" and almost an order of magnitude greater than the flow rate generated in the D-Tek. Further, unlike the Top Gun detector, the sample flow path of the present invention subjects the sensing device to the full, high, flow rate, thereby significantly increasing the sensitivity of the sensing device and reducing the clearing time. While the present invention has a sample path length (the distance between the opening in the probe tip and the sensing device) similar to or longer than the other detectors, especially those that position the sensing device in proximity to the probe tip, the present invention nevertheless provides a much more efficient sample flow path because there are no wires within the probe to obstruct the flow path (D-TEK and The Informant) and the sensing device is placed in direct communication with the inlet side of the pump (as opposed to the D-TEK, The Intimidator and the Top Gun), thus shortening the distance between the sensing device and the pump, which among other things, eliminates the need to clear out the pump before another sample can be taken. The increased flow rate past the sensing device provides a greater sensing device sensitivity, a reduced response time and a shorter clearing time. In addition, the relatively short distance between the sensing device and the printed circuit board, especially compared to the D-TEK and The Informant, reduces the electrical resistance of the connecting wires which reduces the demand on the battery.

The present invention has an advantage in having a sample flow path assembly that is easy to manufacture, thus reducing the time and costs associated with manufacturing the gas detector. The flexible interconnect between the sensing device and the printed circuit board is short and is exterior to the flow path, eliminating the need to insert lengths of wire through a small diameter flexible tube. In addition, the placement of the flexible interconnect exterior to the flow path eliminates the need for sealing the flow path with either rubber plugs or flexible sealant. The individual components of the sample path assembly are either threaded or press fit together. The flexible interconnect requires soldering only at the sensing device. Tubing inside the detector body is eliminated because the only "tubing" interior of the detector body is the socket stem that directly connects the socket holding the sensing device and the inlet portal of the pump.

In addition, the sample flow path assembly of the present invention is advantageous with regard to maintenance issues. The location of the sensing device at the base of the removable probe allows for easy access and replacement. Additionally, if the probe is damaged, it can be easily removed and replaced. Finally, many of the remaining components of the present invention are modular, which makes replacement of any one component relatively easy. Thus, the present invention provides a more reliable and cost effective gas detector.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A sample flow path assembly for use in a gas detector having a sensing detector for sensing the presence of at least one predetermined gas, and a housing partially enclosing the sample flow path assembly, the sample flow path assembly comprising:
   a pump having an outlet and an inlet port;
   a socket connected to the pump, the socket comprises a body and stem portion, the body portion having a front face and a back face opposite the front face, with the sensing device being disposed upon the front face and the back face molded to the stem portion, and with the stem portion opposite the back face of the body portion being inserted into the inlet port of the port of the pump and a continuous opening extending through the socket from the front face of the body portion to the stem portion inserted into the inlet port of the pump;
   a collar disposed around the socket; and
   a probe attached to the collar, the sample flow path providing an unobstructed sample air flow to the sensing device.

2. The sample flow path assembly according to claim 1, wherein the socket further comprises:
   a plurality of holes within the body portion having one opening at the front face and a second opening at the back face.

3. The sample flow path assembly according to claim 2, wherein a plurality of pin receptacles is disposed in the plurality of holes, the plurality of pin receptacles extending from the front face of the socket and protruding beyond the back face of the body portion of the socket.

4. The sample flow path assembly according to claim 1, wherein the body portion and the stem portion of the socket are cylindrically shaped with the stem portion having an outer diameter smaller than an outer diameter of the body portion.

5. The sample flow path assembly according to claim 1, wherein an O-ring is disposed around the stem portion of the socket such that the O-ring is engaged when the stem portion of the socket is inserted into the inlet port of the pump, thereby providing a leakage free connection between the socket and the pump.

6. The sample flow path assembly according to claim 3, wherein a first end of a flexible interconnect is fixedly attached to a portion of each of the plurality of pin receptacles protruding from the back face of the body portion of the socket.

7. The sample flow path assembly according to claim 6, wherein the first end of the flexible interconnect is soldered to the protruding portion of each of the plurality of pin receptacles.

8. A sample flow path assembly for use in a gas detector having a sensing device for sensing the presence of at least one predetermined gas, and a housing partially enclosing the sample flow path assembly, the sample flow path assembly comprising:

a pump;

a socket connected to the pump;

a collar disposed around the socket; and a probe attached to the collar, the sample flow path assembly providing an unobstructed sample air flow to the sensing device, the probe further comprises a probe tip, a flexible outer tube having a first end and a second end, a first bushing attached to the first end of the flexible outer tube for removably attaching the probe to the collar, a second bushing attached to the second end of the flexible outer tube for removably attaching the probe tip to the flexible outer tube and an inner tube disposed within the flexible outer tube, the inner tube being fastened to the first bushing and terminating at the second bushing.

9. The sample flow path assembly according to claim 8, wherein the inner tube is formed from TEFLON®.

10. A method of constructing a sample flow path assembly, the steps comprising:

inserting a body portion of a socket into an opening in a collar;

aligning a front face of the body portion with a front end of the collar;

inserting a stem portion of the socket into an inlet port of a pump;

installing the pump, socket and collar within a first part of a detector body;

positioning a second part of the detector body relative to the first part of the detector body and fastening the first and second portions of the detector body together, the front face of the socket being disposed to be accessible from exterior of the detector body; and attaching a probe to the collar with the probe extending beyond the detector body.

11. The method according to claim 10, further comprising the step of inserting a plurality of pin receptacles into a plurality of pin holes extending between the front face and a back face of the body portion of the socket, a first end of each of the plurality of pin receptacles in approximate alignment with the front face of the body portion of the socket and a second end of each of the plurality of pin receptacles protruding beyond the back face of the body portion of the socket.

12. The method according to claim 11, further comprising the steps of attaching a first end of a flexible interconnect to the protruding portion of each of the plurality of pin receptacles; and connecting a second end of the flexible interconnect to a printed circuit board disposed within the first portion of the detector body.

13. The method according to claim 12, wherein the step of attaching the first end of the flexible interconnect to the protruding portion of each of the plurality of pin receptacles is accomplished by soldering.

14. The method according to claim 12, wherein the step of connecting the second end of the flexible interconnect to the printed circuit board includes pressing the second end of the flexible interconnect into a flex circuit connector disposed on the printed circuit board.

15. The method according to claim 10, wherein the step of inserting socket into the inlet port of the pump includes the steps of inserting a stem portion of the socket into a duct projecting from the inlet port of the pump; and placing an O-ring around the stem section of the socket prior to inserting the stem portion into the duct to prevent leaks between the stem portion and the duct.

16. The method according to 10, further comprising the step of pressing a sensing device onto the front face of the socket before connecting the probe to the collar.

17. The method according to claim 16, wherein the step of pressing the sensing device onto the front face of the socket includes establishing an electrical connection between the pin receptacles and pins integral to the sensing device.

18. The method according to claim 10, wherein the step of attaching the probe to the collar includes the step of threading a first end of the probe onto a correspondingly threaded surface of the collar.

* * * * *